Figure 1:
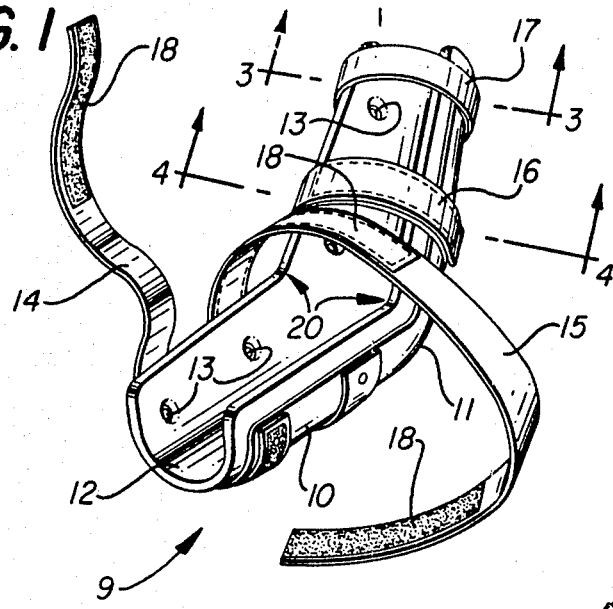

United States Patent [19]

Blackwood et al.

[11] Patent Number: 4,489,716
[45] Date of Patent: Dec. 25, 1984

[54] HYPEREXTENSION LIMITING ELBOW BRACE

[76] Inventors: Robert L. Blackwood, 1005 S. Main, Farmersville, Tex. 75031; David M. Shapiro, 205 Washington Ave., Apt. 211, Santa Monica, Calif. 90403

[21] Appl. No.: 549,313

[22] Filed: Nov. 7, 1983

[51] Int. Cl.³ .............................................. A61F 5/04
[52] U.S. Cl. .................................. 128/77; 128/87 R
[58] Field of Search .................... 128/77, 87 R, 89 R, 128/90

[56] References Cited

U.S. PATENT DOCUMENTS

| | | | |
|---|---|---|---|
| 3,446,880 | 5/1969 | Enicks | 2/16 |
| 3,795,371 | 1/1974 | Lewis | 128/77 |
| 3,800,789 | 4/1974 | Schloss | 128/90 |
| 3,911,497 | 10/1975 | Lewis, Jr. et al. | 2/16 |

Primary Examiner—John D. Yasko
Attorney, Agent, or Firm—Warren H. Kintzinger

[57] ABSTRACT

An elbow hyperextension limiting arm brace spanning the elbow region when strapped in place on a person's arm holding the arm in a normal partially elbow bent attitude. The brace includes an elongate member of strong, rigid plastic conformed to an arm through the elbow region in a partially bent state and that is transversely curved to partially enclose the arm, and padding material mounted therein, that overlaps the edges of the stiff plastic member, for arm protection. A plurality of straps equipped with interconnect structure, such as Velcro interconnect material, are fastened to the arm brace to strap hold the brace in place on the arm.

6 Claims, 6 Drawing Figures

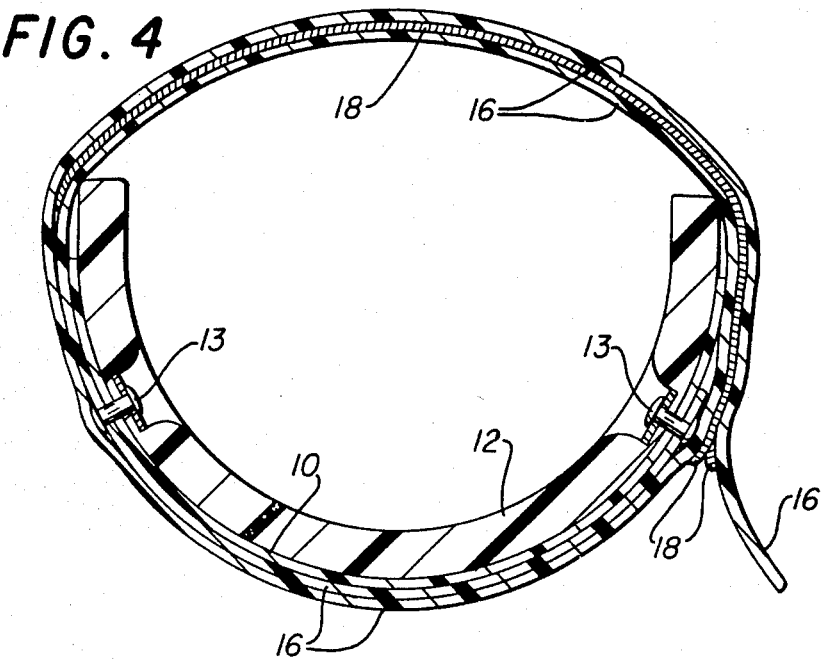
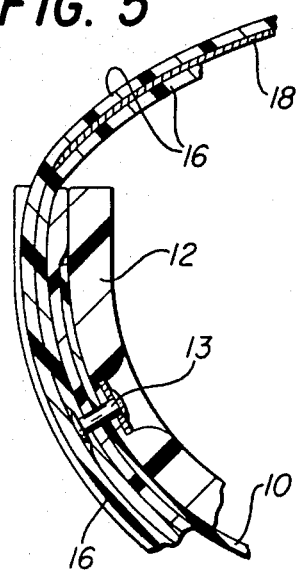
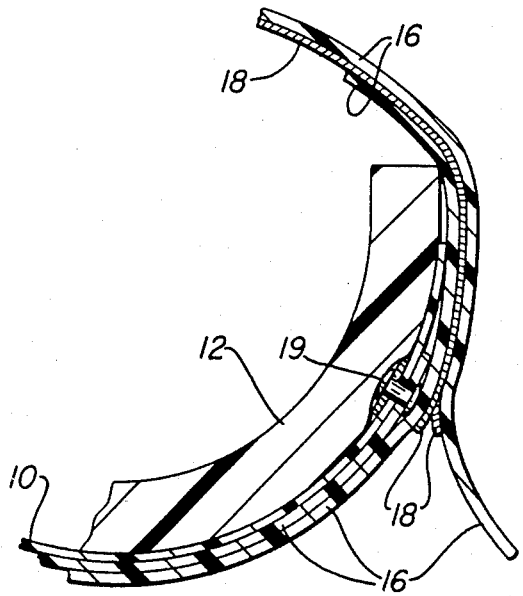

HYPEREXTENSION LIMITING ELBOW BRACE

This invention relates in general to athletic and sports equipment and, in particular, to an elbow hyperextension limiting arm brace that provides better arm/elbow protection than merely taping the arm for participation in sporting events such as football or rodeos.

In sports where there is likelihood of violent contact between participants or between a participant and the ground, injuries often occur simply because of the sheer magnitude of the force of such contacts or because of nature and direction of forces produced by such contacts on the bodies of participants. One common form of injury is an elbow injury such as a hyperextension of the elbow joint. Adhesive taping or other inflexible bracing have been used in attempts to prevent such injury. Such protective means are often quite uncomfortable either because of their weight or their tendency to limit or cut off blood circulation in the arm of the wearer.

It is one object then of the present invention to provide a lightweight reasonably flexible arm/elbow protective brace.

It is a further object of the present invention to provide an arm/elbow protective brace of greater wearing comfort than prior art devices.

It is still a further object of the present invention to provide an arm/elbow protective device which is easily put on or taken off by the user.

The present invention features a single piece plastic brace member of a "cupped" shape which includes an angled bend to receive and the wearer's arm on either side of the elbow joint with the elbow in a partially bent position. The plastic brace is lined with padding and held in position by flexible straps. Because of the particular design of the brace it allows the wearer to flex his elbow to some degree but prevents the elbow from being bent too far backwards (hyperextended).

A specific embodiment representing what is presently regarded as the best mode of carrying out the invention is illustrated in the accompanying drawings.

Figure 2:
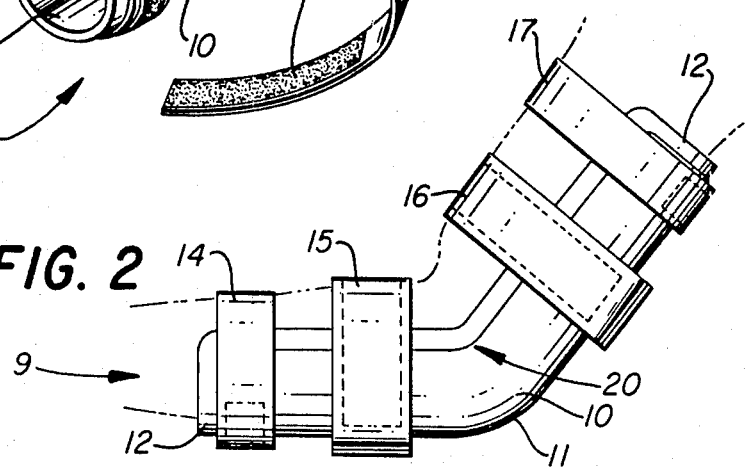
Figure 3:
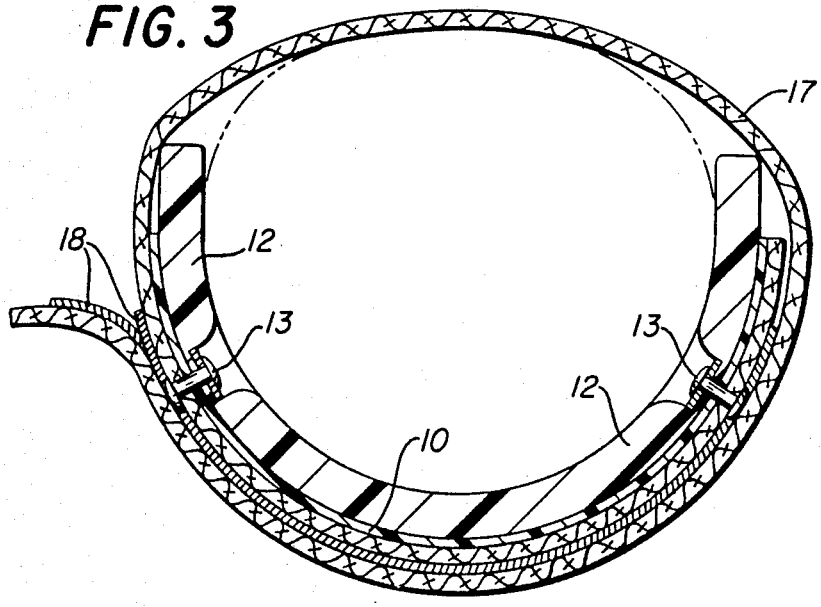

In the drawings:

FIG. 1 is a perspective view of the elbow/arm brace of the present invention;

FIG. 2, a side view of the brace of the present invention illustrating the manner in which it is worn by a user;

FIG. 3, a view in section of the brace taken along lines 3—3 of FIG. 1;

FIG. 4, a view in section of the brace taken along lines 4—4 of FIG. 1;

FIG. 5, a partial view in section similar to FIG. 4 illustrating one technique of mounting the liner padding and retention strips of the brace; and, FIG. 6 is another partial view section similar to FIG. 4 illustrating an alternative technique of mounting the liner padding and retention strips of the present invention.

Referring to the drawings:

The brace of the present invention, designated generally as 9, comprises a lightweight plastic base member 10 that because of its shape may be flexed much more in one direction than the other with very limited flexing. The base member 10 is generally "cupped" or "U" shaped in cross section along its entire length, as can be seen from the figures, such as to prohibit any transverse flexing of the brace. At about its midpoint 11 the base member 10 is angled or bent to about the same extent as a partially bent elbow. This bend may advantageously be between about thirty and about seventy degrees, with about fifty degrees having been found quite comfortable for most wearers. Lining the base member 10 is a padding material 12 that may be foamed or sponge rubber. The padding material 12 may be affixed to the base member 10 by an adhesive glue or other means, or it may be held in place by rivets 13 as illustrated in FIGS. 1, 3, 4 and 5.

The brace is held in position on the wearer preferrably by restraining straps 14,15,16 and 17. The restraining straps may be buckled or fastened by other conventional means but it has been found most advantageous to use a well-known material sold under the brand name Velcro, that is installed on the straps in the areas indicated by 18. The restraining straps may be of any suitable material but it has been found advantageous for the straps 15 and 16 to be of leather, plastic or canvas webbing and for straps 14 and 17 to be of heavy elastic. This material has been found more comfortable for the wearer since it has some degree of give when he attempts to bend his elbow more. All of the restraining straps may be affixed to the base member 10 by the same rivets holding the lining pad 12 or, as shown in FIG. 6, by rivets 19 used only for holding the straps.

It should be pointed out at this point that action of the brace of the present invention is preventing hyperextension of the wearer's elbow is not due solely, or perphaps even principally, to the stiffness of the plastic in the base member 10. Because of its "U" shaped cross section and bend at 11, attempts by the wearer or other forces to straighten his elbow, i.e., straighten the brace from the bend at 11 the edges areas of the plastic opposite the bend 11, indicated in the drawings by the reference number 20, will be put in tensil stress to that such reverse flexing is very limited until the material tears or separates. On the other hand, when forces tend to increase the bend, i.e., the wearer attempts to bend his elbow further, the area 20 is put in compressive stress which is easily relieved by moving outward and beginning to fold double thus allowing the bend of the brace to increase. Thus there has been disclosed a preferred embodiment of a lightweight elbow brace for the prevention of elbow hyperextension.

Whereas this invention is herein illustrated and described with respect to a specific embodiment thereof, it should be realized that various changes may be made without departing from essential contributions to the art made by the teachings hereof.

We claim:

1. An elbow brace comprising: a one-piece base member of semi-stiff bendable plastic shaped to have two ends and a generally "U" shaped cross section along its length and a pre-formed bend about midway of its length thereby to conform generally to a wearer's arm partially bent at the elbow; a resilient cushion material lining the inside surface of said base member; a first pair of restraining strap members each affixed to said base member near respective ends thereof; and a second pair of restraining strap members each fastened to said base at opposite sides of the bend thereof and nearer to the bend than the first straps, with all of said restraining straps adapted to encircle the arm of a wearer and hold it firmly engaged with said brace; and wherein said first pair of restraining strap members is of flexible essentially inelastic material and said second pair of restraining strap members is of flexible elastic material.

2. The elbow brace of claim 1, wherein said bend is at an angle of between thirty and seventy degrees.

3. The elbow brace of claim 2, wherein said bend is at an angle of about fifty degrees.

4. The elbow brace of claim 1, wherein said essentially inelastic material is leather.

5. The elbow brace of claim 1, wherein said essentially inelastic material is canvas webbing.

6. The elbow brace of claim 1, with said restraining straps including interconnect material positioned to hold overlapped strap ends together when the restraining straps are wrapped around an arm.

* * * * *